(12) United States Patent
Takekoshi et al.

(10) Patent No.: US 8,379,796 B2
(45) Date of Patent: Feb. 19, 2013

(54) RADIATION IMAGING APPARATUS, RADIATION IMAGING METHOD, RADIATION IMAGE PROCESSING APPARATUS, RADIATION IMAGE PROCESSING METHOD, AND COMPUTER-READABLE STORAGE MEDIUM

(75) Inventors: Koji Takekoshi, Yokohama (JP); Tsukasa Sako, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 245 days.

(21) Appl. No.: 12/869,885

(22) Filed: Aug. 27, 2010

(65) Prior Publication Data
US 2011/0075812 A1 Mar. 31, 2011

(30) Foreign Application Priority Data
Sep. 25, 2009 (JP) ................................. 2009-221445

(51) Int. Cl.
*H05G 1/64* (2006.01)
(52) U.S. Cl. ........................... 378/98; 378/98.2; 378/115
(58) Field of Classification Search .................... 378/62, 378/91, 98, 98.2, 98.5, 98.8, 115
See application file for complete search history.

(56) References Cited

FOREIGN PATENT DOCUMENTS
JP 2000-217808 8/2000

OTHER PUBLICATIONS
FDA Part 1020 Sec. 1020.32 Fluoroscopic Equipment, Jun. 2005.

*Primary Examiner* — Jurie Yun
(74) *Attorney, Agent, or Firm* — Fitzpatrick, Cella, Harper & Scinto

(57) ABSTRACT

A radiation imaging apparatus includes an imaging unit to capture a radiation image of an object, a discrimination unit to discriminate whether the current imaging mode is a mode of storing radiation images or a mode of storing no radiation image, a first calculation unit to calculate image size information, a second calculation unit to calculate image display region information indicating the size of an image display region, a first decision unit to decide a rotation condition for the rotation of an displayed image, and a second decision unit to decide an enlargement/reduction condition. If discriminated at the start of radiation irradiation that the current mode is the mode of storing no image, the second decision unit decides an enlargement/reduction condition from image size information and image display region information to maximize the ratio of an overall radiation image rotated under the rotation condition decided.

21 Claims, 7 Drawing Sheets

F I G. 6A   MODE OF STORING NO IMAGE

|  | START OF IRRADIATION | DURING IRRADIATION | PERIOD OTHER THAN PERIOD OF IRRADIATION |
|---|---|---|---|
| ROTATION | SAME CONDITIONS AS FINAL CONDITIONS FOR PREVIOUSLY CAPTURED IMAGE | ROTATION PROCESSING BASED ON USER OPERATION | ROTATION PROCESSING BASED ON USER OPERATION |
| ENLARGEMENT/ REDUCTION | FIT DISPLAY | FIT OR FIT PROCESSING BASED ON ROTATING OPERATION | ENLARGEMENT/REDUCTION PROCESSING BASED ON USER OPERATION |
| PANNING | CANCEL (NO) | NO PROCESSING BECAUSE OF FIT | PANNING PROCESSING BASED USER OPERATION |

F I G. 6B   MODE OF STORING IMAGES

|  | START OF IRRADIATION | DURING IRRADIATION | PERIOD OTHER THAN PERIOD OF IRRADIATION |
|---|---|---|---|
| ROTATION | SAME CONDITIONS AS FINAL CONDITIONS FOR PREVIOUSLY CAPTURED IMAGE | ROTATION PROCESSING BASED ON USER OPERATION | ROTATION PROCESSING BASED ON USER OPERATION |
| ENLARGEMENT/ REDUCTION | SAME CONDITIONS AS FINAL CONDITIONS FOR PREVIOUSLY CAPTURED IMAGE | ENLARGEMENT/REDUCTION PROCESSING BASED ON USER OPERATION | ENLARGEMENT/REDUCTION PROCESSING BASED ON USER OPERATION |
| PANNING | SAME CONDITIONS AS FINAL CONDITIONS FOR PREVIOUSLY CAPTURED IMAGE | PANNING PROCESSING BASED USER OPERATION | PANNING PROCESSING BASED USER OPERATION |

F I G. 6C  STILL IMAGE MODE

| | START OF IRRADIATION | DURING IRRADIATION | PERIOD OTHER THAN PERIOD OF IRRADIATION |
|---|---|---|---|
| ROTATION | DEFAULT PARAMETERS | DEFAULT PARAMETERS | ROTATION PROCESSING BASED ON USER OPERATION |
| ENLARGEMENT/ REDUCTION | DEFAULT PARAMETERS | DEFAULT PARAMETERS | ENLARGEMENT/REDUCTION PROCESSING BASED ON USER OPERATION |
| PANNING | DEFAULT PARAMETERS | DEFAULT PARAMETERS | PANNING PROCESSING BASED USER OPERATION |

F I G. 6D  MODE OF STORING NO IMAGE

| | START OF IRRADIATION | DURING IRRADIATION | PERIOD OTHER THAN PERIOD OF IRRADIATION |
|---|---|---|---|
| ROTATION | SAME CONDITIONS AS FINAL CONDITIONS FOR PREVIOUSLY CAPTURED IMAGE | ROTATION PROCESSING BASED ON USER OPERATION | ROTATION PROCESSING BASED ON USER OPERATION |
| ENLARGEMENT/ REDUCTION | FIT DISPLAY | ENLARGEMENT/REDUCTION PROCESSING BASED ON USER OPERATION WITHIN RANGE OF NUMBER OF PIXELS OF IMAGE DISPLAY REGION | ENLARGEMENT/REDUCTION PROCESSING BASED ON USER OPERATION |
| PANNING | CANCEL (NO) | PANNING PROCESSING BASED ON USER OPERATION WITHIN RANGE OF NUMBER OF PIXELS OF IMAGE DISPLAY REGION | PANNING PROCESSING BASED USER OPERATION |

RADIATION IMAGING APPARATUS, RADIATION IMAGING METHOD, RADIATION IMAGE PROCESSING APPARATUS, RADIATION IMAGE PROCESSING METHOD, AND COMPUTER-READABLE STORAGE MEDIUM

BACKGROUND OF THE INVENTION

1. Field of the Invention

The present invention relates to a radiation imaging apparatus, radiation imaging method, radiation image processing apparatus, radiation image processing method, and computer-readable storage medium.

2. Description of the Related Art

In the field of image diagnosis using radiation imaging apparatuses and more particularly X-ray imaging apparatuses, an image intensifier (to be also referred to as an "I.I." hereinafter)-TV system has been widely used. Recently, there has been proposed a radiation imaging apparatus using a solid-stage radiation (for example, X-rays) detector with a high resolution which uses an FPD (Flat Panel Detector) in place of an image intensifier. A captured image obtained by an I.I. is circular. In contrast, a radiation imaging apparatus using an FPD allows to increase the effective field of view as compared with an I.I. because the FPD is a quadrangular flat panel detector (having, for example, a rectangular shape).

In a radiation imaging apparatus using a conventional I.I., even when the detector unit rotates or an image on the display device rotates, since the radiation irradiation region to be displayed has a circular shape, the rotation does not change the effective display region. That is, no problem has arisen. For example, Japanese Patent Laid-Open No. 2000-217808 discloses an invention which copes with the rotation of a detector by using a display rotation system to rotate a TV monitor. Matching with the image reception area of a radiation irradiation field is defined by an industrial standard in "JIS Handbook 2005 Radiation (Activity)", C0601-1-3 medical electrical equipment: Japanese Standards Association, section 29.203.4 and FDA Part 1020 Sec. 1020.32 Fluoroscopic equipment.

However, the radiation imaging apparatus using the above FPD has the following problems.

FIG. 2A shows a case in which a quadrangular flat panel detector performs display operation so as to match the vertical and horizontal directions of an image display region on a display device with those of the quadrangular flat panel detector. An image 201 is the radiation image detected by the quadrangular flat panel detector. An auxiliary view 202 represents the relative positional relationship between the object and the quadrangular flat panel detector. In this case, depending on the positional relationship between the object and the quadrangular flat panel detector, the user may want to display an image upon rotating it. For example, referring to FIG. 2B, the auxiliary view 202 is obliquely displayed. This occurs when, for example, the relative positional relationship between the object and the quadrangular flat panel detector has an error or the vertical and horizontal directions of the quadrangular flat panel detector do not match those of the display device. At this time, if, for example, as shown in FIG. 2C, the image is rotated to an orientation that allows easy observation while the display magnification of the image is maintained, there are some regions which are not displayed on the display device. That is, there is a possibility that the image data detected by the quadrangular flat panel detector may be partly lost by rotating operation. In order to prevent such data loss, display conditions need to be adjusted as shown in FIG. 2D.

In general, a radiation imaging apparatus is provided in advance with a mode of storing captured images and a mode of storing no image. For example, in an imaging mode called fluoroscopy, no captured image is stored in the imaging apparatus. On the other hand, in imaging modes other than fluoroscopy, for example, the serial radiography and cine modes, all types of images are targets to be stored. The mode of storing no image is used for a postoperative checkup on a patient after surgical operation or positioning or timing adjustment for still image capturing. This mode is rather a mode of checking an image on the spot. In contrast, each mode of storing images is often used for the purpose of performing detailed diagnosis afterward by using stored images. As described above, in the mode of storing no image, the user wants to display the entire radiation irradiation region, and hence wants to avoid the loss of part of image data by rotating operation. In contrast, in the mode of storing images, since the user wants to continuously display a region of interest on the screen, the user wants to easily check the region of interest. That is, the timing and contents of image checking operation differ depending on the purpose of imaging. For this reason, setting the same conditions for deciding an image display form such as rotational display, enlarged/reduced display, panning display (display with movement of image center), or the like makes it difficult to obtain a desired observation image.

In consideration of the above problems, the present invention provides a technique of displaying the radiation image captured by using a quadrangular flat panel detector in a display form corresponding to each purpose of imaging by controlling the display form of an image in accordance with each purpose of imaging in the imaging mode of storing images and the imaging mode of storing no image.

SUMMARY OF THE INVENTION

According to one aspect of the present invention, there is provided a radiation imaging apparatus comprising:

an imaging unit adapted to capture a radiation image of an object;

a discrimination unit adapted to discriminate whether an imaging mode of the radiation image captured by the imaging unit is a mode of storing the radiation image in a storage unit or a mode of not storing the radiation image in the storage unit;

a first calculation unit adapted to calculate image size information indicating a size of the radiation image;

a second calculation unit adapted to calculate image display region information indicating a size of an image display region in which the radiation image is configured to be displayed by the display unit;

a first decision unit adapted to decide a rotation condition for rotation of the radiation image when the radiation image captured by the imaging unit is displayed on the display unit; and a second decision unit adapted to decide an enlargement/reduction condition for display of the radiation image upon enlargement or reduction thereof when the radiation image captured by the imaging unit is displayed on the display unit, wherein if the discrimination unit discriminates at the start of radiation irradiation by the imaging unit that an imaging mode of the radiation image captured by the imaging unit is the mode of not storing the radiation image, the second decision unit decides the enlargement/reduction condition from the image size information and the image display region information such that the overall radiation image rotated under a rotation condition decided by the first decision unit is displayed at a maximum ratio with respect to the image display region.

According to the present invention, it is possible to display the radiation image captured by using the quadrangular flat panel detector in a display form corresponding to each purpose of imaging by controlling the display form of an image in accordance with each purpose of imaging in the imaging mode of storing images and the imaging mode of storing no image.

Further features of the present invention will become apparent from the following description of exemplary embodiments (with reference to the attached drawings).

BRIEF DESCRIPTION OF THE DRAWINGS

FIGS. 6A to 6D are views showing display conditions under which the present invention can be implemented.

DESCRIPTION OF THE EMBODIMENTS

First Embodiment

Figure 1:
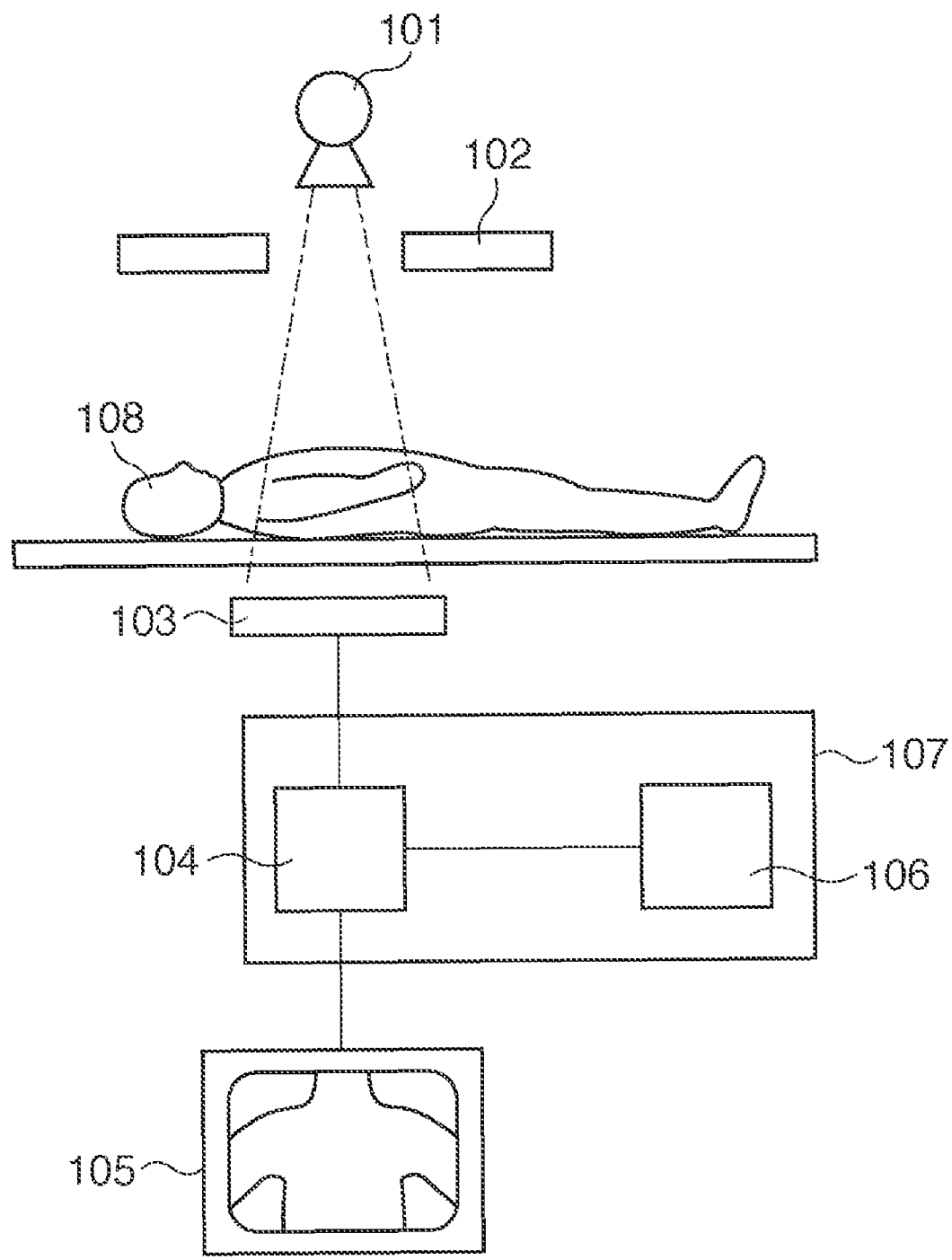
FIG. 1 is a view showing the functional arrangement of a radiation imaging apparatus.
Figure 2A:
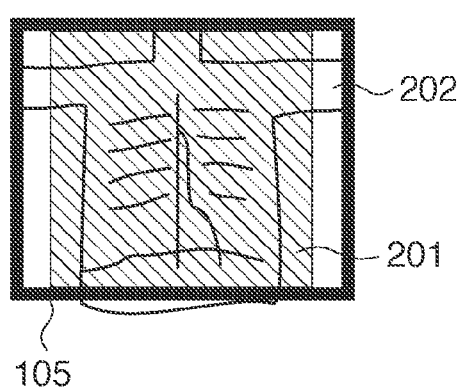
FIGS. 2A to 2D are views showing the relative positional relationship between an object and a detector.
Figure 2B:
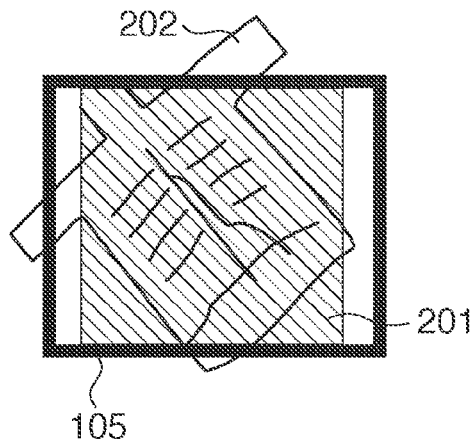
Figure 2C:
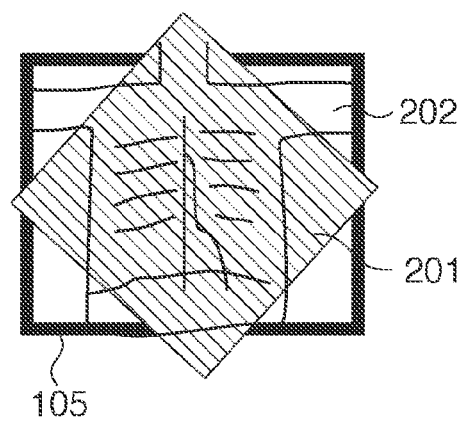
Figure 2D:
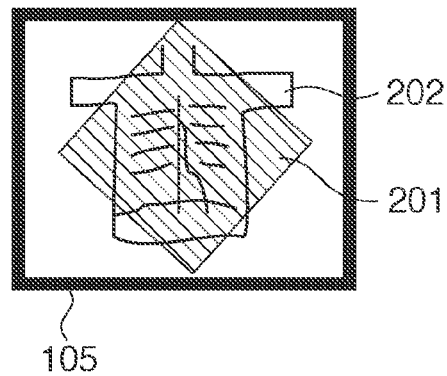

The schematic arrangement of a radiation imaging apparatus using an FPD according to the present invention will be described with reference to FIG. 1. This apparatus irradiates an object 108 with the radiation emitted from a radiation tube 101 through a radiation stop 102. The apparatus then detects the radiation transmitted through the object 108 through a detector unit 103, and converts the radiation into an image signal. The apparatus is configured to process the converted image signal by using an image processing unit 104 and display the resultant data as an image on a display device 105. The radiation with which the object 108 is irradiated passes through the radiation stop 102 to irradiate only a predetermined range necessary for imaging. The detector unit 103 converts the radiation transmitted through the object 108 into an optical image of visible light using a phosphor in the detector unit 103, and then converts the optical image into an image signal. The image processing unit 104 converts an input image signal into digital image data, and performs various kinds of computation and image processing, for example, image enlargement/reduction, movement of an image position, and the addition/subtraction of image data. A storage device 106 records and archives digital image data before or after image processing. The storage device 106 can not only store a moving image captured by irradiating radiation but also archive a still image captured at an arbitrary timing while observing a moving image. A controller 107 controls the radiation imaging apparatus, for example, the radiation tube 101, the detector unit 103, and the display device 105, and comprehensively controls the overall radiation imaging apparatus. The controller 107 includes the image processing unit 104 and the storage device 106.

The relative positional relationship between the object 108 and the detector unit 103 in this radiation imaging apparatus allows rotation. "Rotation" in this case means rotation about the center of the detector unit 103 as an axis within a plane including the detection surface of the detector unit 103, but does not indicate that the detector unit 103 rotates about the center axis of the object 108.

Figure 3:
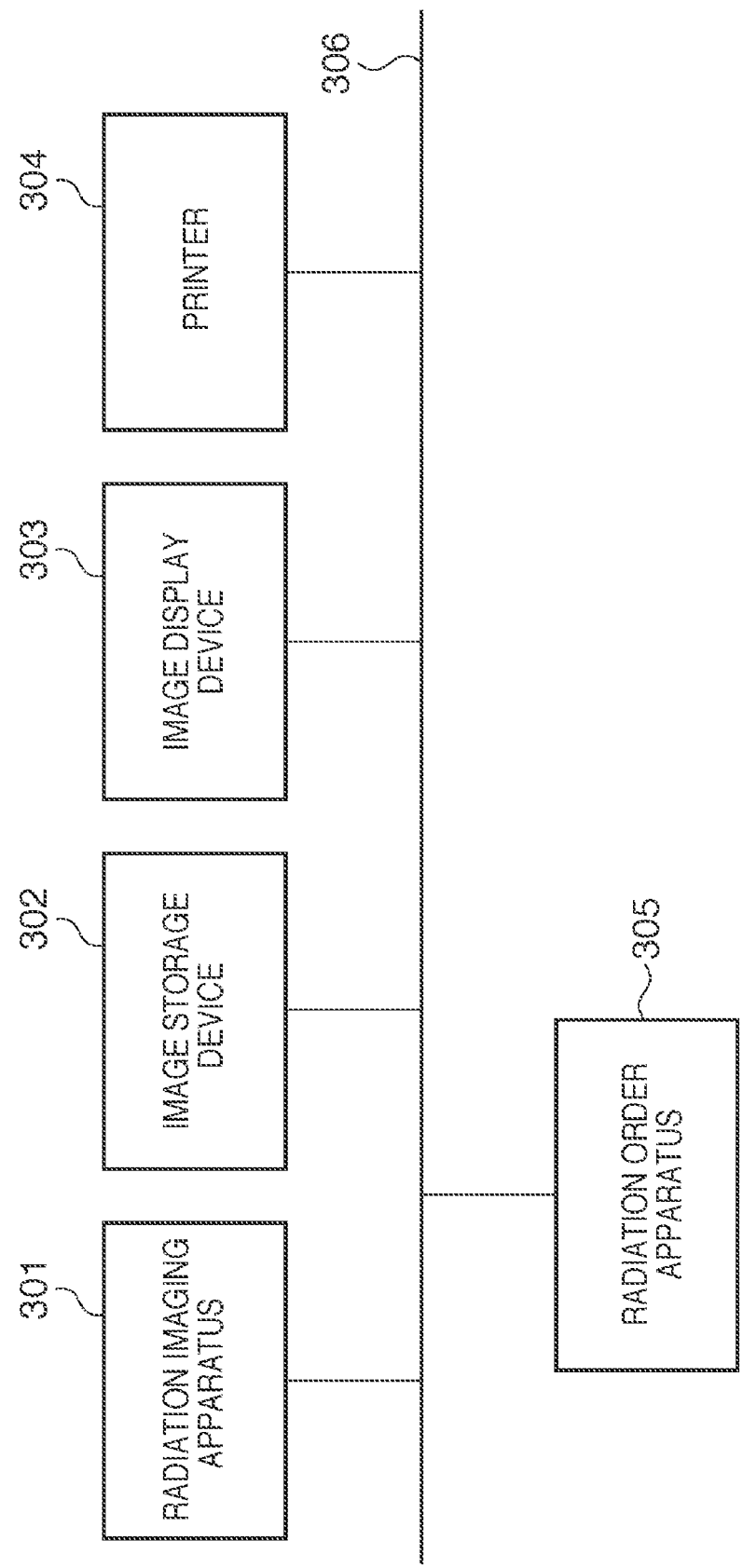
FIG. 3 is a block diagram of the system of the radiation imaging apparatus.

An example of the arrangement of a radiation imaging system according to the present invention will be described next with reference to FIG. 3. A radiation imaging apparatus 301 is a medical imaging apparatus to perform radiation imaging or the like. This system includes a radiation CT apparatus and an MRI apparatus, which are also called modalities. Referring to FIG. 1, the radiation imaging apparatus includes the display device 105 and the storage device 106. However, as shown in FIG. 3, an image storage device 302, an image display device 303, and the like may be arranged outside the radiation imaging apparatus 301. The image storage device 302 stores the image captured by the radiation imaging apparatus 301, and is called a PACS (Picture Archiving and Communications Systems). The image display device 303 displays the image captured by the radiation imaging apparatus 301 for image diagnosis. A printer 304 prints a radiation image on a printing medium such as a film or paper. Note that the apparatus may not include the printer 304 when being applied to film-less operation. A radiation order apparatus 305 is an apparatus which issues an imaging order, and is also called an RIS (Radiology Information Systems). These apparatuses are connected to each other via a network 306.

Figure 4:
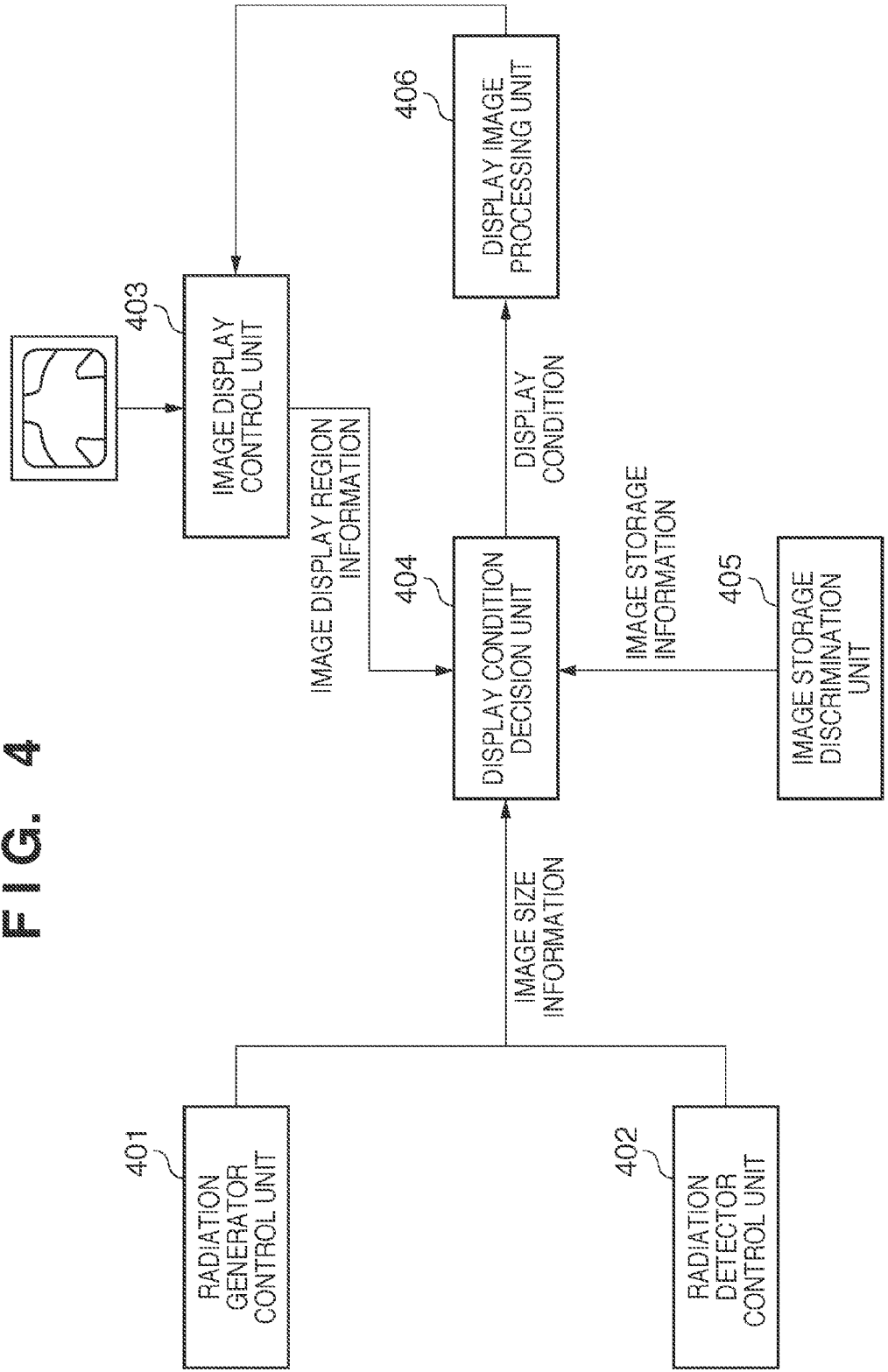
FIG. 4 is a block diagram of a control arrangement for the radiation imaging apparatus.

The functional arrangement of the radiation imaging apparatus will be described next with reference to FIG. 4. A radiation generator control unit 401 controls the radiation tube 101 like that shown in FIG. 1. A radiation detector control unit 402 controls the detector unit 103 like that shown in FIG. 1, which functions as a radiation detection unit. An image display control unit 403 controls the display of an image on the display device 105 like that shown in FIG. 1 (the image display device 303 in the case of the apparatus arrangement in FIG. 3), which functions as an image display unit. A display condition decision unit 404 functions as the first decision unit to decide rotation conditions for the rotation of an image, the second decision unit to decide enlargement/reduction conditions for an image, and the third decision unit to decide panning conditions for panning display (display with movement of image center). Note that each decision unit may be a computer-human interface such as a keyboard or mouse (not shown). An image storage discrimination unit 405 discriminates whether the current mode is the mode of storing captured radiation images in the storage device 106 (or the image storage device 302). A display image processing unit 406 executes image processing for an image to be displayed under decided rotation conditions, enlargement/reduction conditions, and panning conditions. This image processing includes general image processing such as brightness adjustment and contrast adjustment in addition to geometric transformation. The processing units 401 to 406 mainly execute each process in the flowchart shown in FIG. 5 (to be described later). The storage device 106 also stores the rotation conditions, enlargement/reduction conditions, and panning conditions decided by the respective decision units described above.

Figure 5:
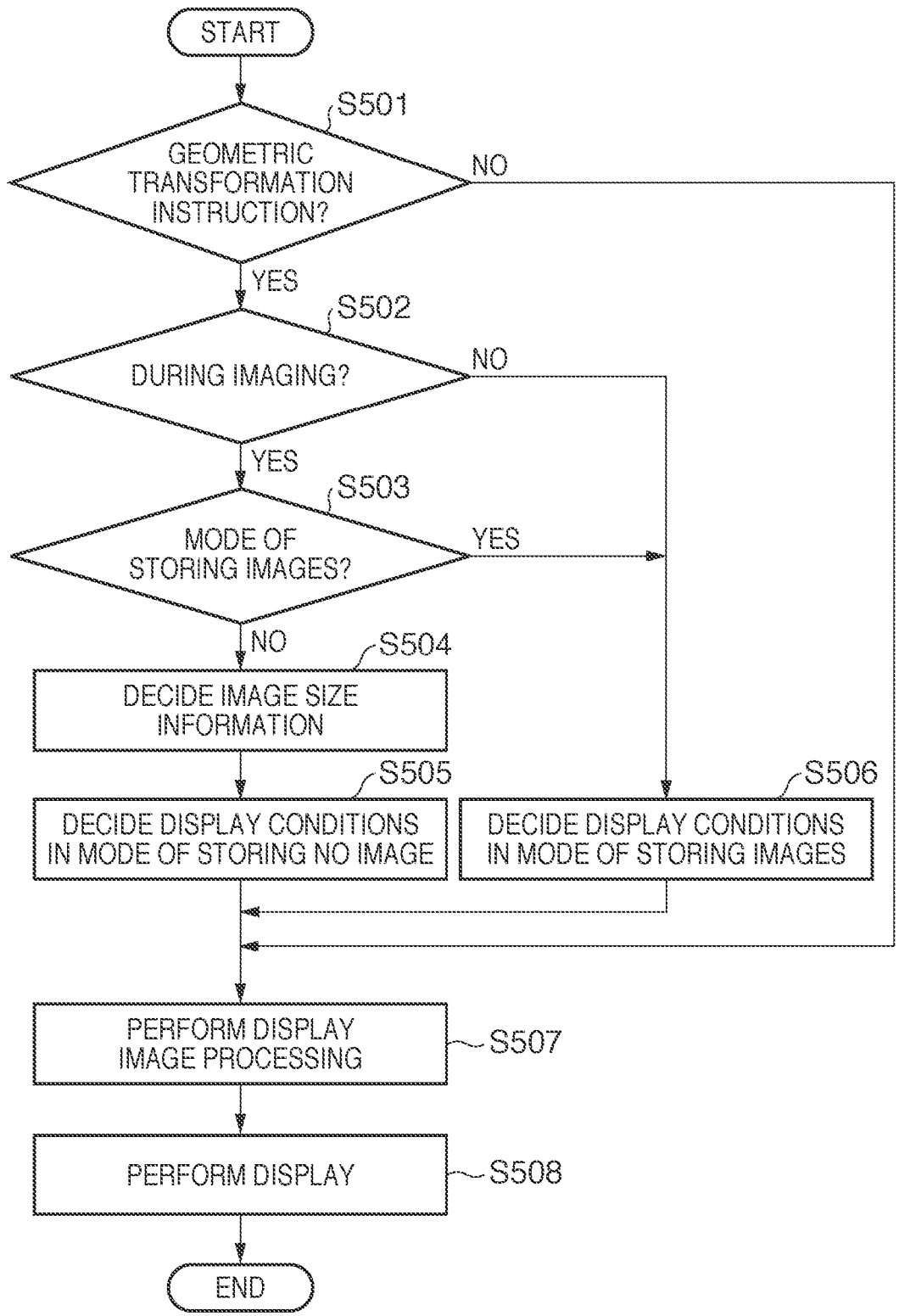
FIG. 5 is a flowchart which can implement the present invention.

A processing procedure in the radiation imaging apparatus according to this embodiment will be described with reference to FIG. 5. First of all, in step S501, this apparatus discriminates whether the user has input a geometric transformation instruction via an input device (not shown). Geometric transformation indicates, for example, enlargement/ reduction processing, rotation processing, or panning processing. If there is no change in geometric transformation processing, the display conditions are the same as those at the previous imaging operation. If, therefore, there is no change, it is possible to use the same condition values as those used in the previous image operation. Note that it is possible to start operation from the processing in step S502 without performing the processing in step S501. If there is a geometric transformation instruction (YES in step S501), the process advances to step S502. If no geometric transformation instruction is input (NO in step S501), the process advances to step S507. In step S502, the apparatus discriminates whether the radiation imaging apparatus 301 is performing imaging. If the radiation imaging apparatus 301 is performing imaging (YES in step S502), the process advances to step S503. If the radiation imaging apparatus 301 is not performing imaging (NO in step S502), the process advances to step S506. In step S503, the image storage discrimination unit 405 discriminates whether the type of imaging mode is the imaging mode of storing images or the imaging mode of storing no image. The imaging mode of storing images is the imaging mode of the radiation imaging apparatus 301 which stores all the images captured by the radiation imaging apparatus 301 in the storage device 106. The storage device 106 is the hard disk drive of a general computer. However, the storage device 106 may be a device other than the hard disk drive as long as the device is a storage device which the computer can handle. The imaging mode of storing no image is the mode of storing no image in the storage device 106, and includes, for example, imaging called fluoroscopy. In fluoroscopy, when irradiating radiation, the apparatus displays the captured image on the display device in real time but does not store the image. Note however that it is possible to store only the final image in fluoroscopy or store only an image which exists in the memory of the computer and can be stored in response to an instruction from the user after imaging. The imaging mode of storing images includes still image capturing, cine capturing, DA, and DSA. All the images acquired by these imaging operations are stored in the storage device 106. When these imaging operations are classified according to moving images and still images, fluoroscopy, cine capturing, DA, and DSA are moving image capturing modes, and still image capturing is obviously a still image capturing mode. If the imaging mode is the mode of storing images (YES in step S503), the process advances to step S506. If the imaging mode is the mode of storing no image (NO in step S503), the process advances to step S504.

<Mode of Storing No Image>

In step S504, the apparatus decides image size information. There are two image size information decision methods including a method of deciding image size information based on image data information and a method of deciding image size information based on collimator position information.

First of all, the method of deciding an image size based on image data information is the method of deciding the image data size received from the detector unit 103 in FIG. 1 as an image size. The detection conditions set for the detector unit 103 includes detection region information. The detection conditions set for the detector unit 103 include various detection conditions for detection with the entire region of a sensor forming the detector unit 103, detection with a detection region having a size of 14 inches (vertical)×17 inches (horizontal), and detection with a detection region having a size of 9 inches (vertical)×9 inches (horizontal). A detection region is decided under these detection conditions. The data obtained by reading the detection region is handled as image data. If, therefore, a detection region is decided, an image size is confirmed. Since the detector unit 103 transmits the confirmed image size information to the radiation detector control unit 402, the radiation detector control unit 402 functioning as the first calculation unit can calculate an image size based on the received image size information. It is also possible to discriminate an image size before the reception of an image. In this case, an image size is decided from the detection conditions set for the detector unit 103. If, for example, detection is to be performed with a size of 14 inches×17 inches, it is possible to decide an image size, like 2208×2688, from the related information of the detection region and image size. It is also possible to decide an image size by calculating the numbers of pixels in the vertical and horizontal directions from the pixel pitches of the detection region and sensor.

The method of deciding an image size from collimator position information is the method of calculating an image size from the collimator position information of the radiation generator control unit 401 functioning as the first calculation unit. The collimator is a stop mechanism for deciding a radiation irradiation field. Narrowing the irradiation region will limit the region irradiated with radiation. This will also limit the effective region as an image. This limited region is image size information. It is therefore possible to calculate image size information from the collimator position information of the radiation generator control unit 401. Although an image size cannot be decided before imaging, it may be decided by extracting an irradiation region from a captured image itself by image processing.

If there are both the image size decided from collimator position information and the image size decided from image data information, a smaller one of the image sizes may be decided as image size information. There is some type of radiation generator control unit 401 which cannot notify collimator position information. In this case, an image size is decided from image data information.

In step S505, the display condition decision unit 404 calculates a display magnification in a case in which an image is displayed based on image size information and image display region information. Image display region information is information about a region of an image which can be displayed on the display device 105. A display magnification is calculated as follows. As image size information, the image size information decided in step S504 is used. The image display control unit 403 functioning as the second calculation unit calculates image display region information. When, for example, an image is to be displayed on the display device 105 with its full resolution, a region in which the image can be displayed is decided by the display resolution of the display device 105. In another case, when using an application for presenting an image and patient information and other related information other than the image information with the full resolution of the display device 105, the apparatus sets an image display region in addition to a display region for these pieces of patient information and other related information. For this reason, the apparatus decides a display region based on the display resolution of the display device 105 and image display region conditions for the application.

Operation at the start of radiation irradiation in the mode of storing no image will be described with reference to FIG. 6A. Assume that conditions for the rotation processing of rotating an image are the same as the rotation conditions (final rotation conditions) decided by the display condition decision unit 404 functioning as the first decision unit at the previous radiation imaging. When, for example, performing radiation irradiation in the normal fluoroscopy mode, the apparatus displays a fluoroscopic image of the final frame on the screen. In some case, the user may adjust the rotational angle of the image while referring to the final fluoroscopic image after imaging. Assume that the conditions after the adjustment of rotation conditions are the final rotation conditions (rotation conditions at the next imaging operation) because it is desirable to display the next image in the same state as that of the result obtained by adjusting the rotation conditions. If, for example, the user adjusts an image while referring to a fluoroscopic image, the display processing conditions (final rotation conditions) for the image which has been displayed are confirmed at the instant when the next radiation irradiation starts. Therefore, final rotation conditions are rotation conditions at the end of radiation imaging or adjusted rotation conditions if adjustment is performed after imaging.

The apparatus decides enlargement/reduction conditions based on the image size information decided in step S504 and image display region information such that the image associated with the image size information is displayed in the image display region at the maximum ratio. The enlargement/reduction conditions can additionally include a condition that an image should be displayed within the number of pixels of the image display region. Such display will be referred to as fit display hereinafter. Fit display is a mode of storing no image in the storage device 106, and hence is a display form that displays an overall radiation irradiation region as large as possible. Likewise, there is no panning condition. That is, the image is displayed in the center.

Operation during radiation irradiation in the mode of storing no image will be described with reference to FIG. 6A. Assume that rotation conditions for the rotation of an image are those based on user operation. The reason for this is to allow the user to freely adjust rotation conditions for an image during radiation irradiation. Assume that enlargement/reduction conditions are kept the same as those for fit display as in the case of enlargement/reduction conditions at the start of radiation irradiation. Note that since enlargement/reduction processing during radiation irradiation is kept the same as that for fit display, GUI control may be performed for enlargement/reduction processing so as to reject user operation. Since fit display is maintained, no panning processing is performed. Likewise, GUI control may be performed so as to reject user operation. In some cases, processing is performed under enlargement/reduction conditions as image processing conditions, although user operation for enlargement/reduction is not accepted. The reason for this is to fit-display an image in accordance with that the user can freely change rotation conditions for the image. Therefore, enlargement/reduction processing is performed to perform fit display. That is, enlargement/reduction conditions during radiation irradiation are for the execution of fit display or fit processing in accordance with rotating operation.

Operation during a period other than a period of radiation irradiation in the mode of storing no image will be described with reference to FIG. 6A. The apparatus performs operation during a period other than a period of radiation irradiation in accordance with user operation in terms of all conditions including rotation conditions, enlargement/reduction conditions, and panning conditions.

<Mode of Storing Images>

In step S506, the apparatus decides display conditions for a case in which the imaging mode is the mode of storing images in the storage device 106.

Operation at the start of radiation irradiation in the mode of storing images will be described first with reference to FIG. 6B. Assume that the rotation conditions in this operation are the same as the final rotation conditions decided by the display condition decision unit 404 functioning as the first decision unit in the previous radiation imaging operation. Assume that the enlargement/reduction conditions are the same as the final enlargement/reduction conditions decided by the display condition decision unit 404 functioning as the second decision unit in the previous radiation imaging operation as in the case with the rotation conditions in the mode of storing no image. That is, the final enlargement/reduction conditions are the same as those set at the end of radiation imaging or those having undergone adjustment when adjustment has been performed after imaging. This is because the mode of storing no image gives priority to the operation of displaying an entire radiation irradiation region. In contrast to this, the mode of storing images gives priority to the operation of continuously displaying a region of interest of an image on the screen. Assume that the panning conditions are also the same as the final conditions for panning for the previously captured radiation image. That is, the final panning conditions are those set at the end of radiation imaging or those having undergone adjustment when adjustment has been performed after imaging. Operation during radiation irradiation in the mode of storing images will be described next with reference to FIG. 6B. The apparatus performs processing under processing conditions based on user operation in terms of all conditions including rotation conditions, enlargement/reduction conditions, and panning conditions.

Operation during a period other than a period of radiation irradiation in the mode of storing images will be described with reference to FIG. 6B. The apparatus performs operation under processing conditions based on user operation in terms of all conditions including rotation conditions, enlargement/reduction conditions, and panning conditions. The apparatus also performs processing based on user operation even during a period other than a period of imaging.

In step S507, the display image processing unit 406 performs display image processing of enlargement/reduction, rotation, and panning under the display conditions decided in step S505 (the mode of storing no image) or step S506 (the mode of storing images). Note that it is possible to perform image processing other than these kinds of display image processing. In step S508, the apparatus displays the image processed in step S507 on the display device, and then terminates the processing.

Second Embodiment

In step S505 in the first embodiment, enlargement/reduction conditions are kept the same as those for fit display during radiation irradiation in the mode of storing no radiation image. In contrast, the second embodiment performs enlargement/reduction processing based on user operation within the range of the number of pixels of an image display region, as shown in FIG. 6D. That is, the apparatus can perform operation in a direction to reduce an image from a fit display state at the start of radiation irradiation. It is possible to perform enlargement processing after reduction until fit display. In addition, reduction processing allows panning processing of an image. It is possible to perform panning processing within the range of the number of pixels of an image display region.

Third Embodiment

In the first embodiment, the imaging modes are classified into the mode of storing images and the mode of storing no image. In the third embodiment, imaging modes are classified into a mode of storing no moving image, a mode of storing moving images, and a mode of storing still images. Assume that the processing in steps S505 and S506 in the first embodiment is the following processing.

In step S505 in the first embodiment, rotation processing conditions at the start of radiation irradiation in the mode of storing no image are the same as the final rotation conditions after previous radiation imaging operation (see FIG. 6A). In contrast to this, in the third embodiment, rotation processing conditions at the start of radiation irradiation are the same as the final rotation conditions after the end of radiation imaging in the previous moving image mode.

In step S506 in the first embodiment, rotation conditions and enlargement/reduction conditions at the start of radiation irradiation in the mode of storing images are the same as the final rotation conditions and final enlargement/reduction conditions after the previous radiation imaging operation. The third embodiment uses rotation conditions and enlargement/reduction conditions after radiation imaging in the previous moving image mode.

That is, only the moving image mode inherits the final conditions in the previous imaging operation. Consider a case in which the apparatus has performed the following types of imaging, that is, moving image mode 1 firstly, moving image mode 2 secondly, still image mode 1 thirdly, and moving image mode 3 fourthly. In this case, still image mode 1 performed thirdly operates independently with default parameters. Moving image mode 3 performed fourthly is a moving image mode to inherit conditions, and hence performs display under the same conditions as the final conditions in moving image mode 2 performed secondly.

In addition, as display processing conditions in the still image mode at the start of radiation irradiation and during radiation irradiation, rotation conditions, enlargement/reduction conditions, and panning conditions are all default parameters. Default parameters are processing conditions which the still image capturing mode have in advance. In this case, the display processing conditions are default parameters. However, in order to set default parameters as display processing conditions regardless of user operation, GUI control may be performed so as to reject user operation.

Fourth Embodiment

In this third embodiment, the respective display image processing conditions in each moving image mode are the same as the final conditions for the radiation image captured in the previous moving image mode. The fourth embodiment is configured to decide conditions for each type of moving image mode (imaging classification) such as a fluoroscopy mode, cine mode, DA mode, or DSA mode. That is, the respective display image processing conditions in each moving image mode are the same as the final conditions for the previous radiation image captured in the same imaging classification. Although the fourth embodiment may be applied to all display image processing conditions, the embodiment may be applied to only image processing such as brightness adjustment and contrast adjustment other than geometric transformation.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-221445, filed Sep. 25, 2009, which is hereby incorporated by reference herein in its entirety.

What is claimed is:

1. A radiation imaging apparatus comprising:
an imaging unit adapted to capture a radiation image of an object;
a discrimination unit adapted to discriminate whether an imaging mode of the radiation image captured by said imaging unit is a mode of storing the radiation image in a storage unit or a mode of not storing the radiation image in the storage unit;
a first calculation unit adapted to calculate image size information indicating a size of the radiation image;
a second calculation unit adapted to calculate image display region information indicating a size of an image display region in which the radiation image is configured to be displayed by a display unit;
a first decision unit adapted to decide a rotation condition for rotation of the radiation image when the radiation image captured by said imaging unit is displayed on the display unit; and
a second decision unit adapted to decide an enlargement/reduction condition for display of the radiation image upon enlargement or reduction thereof when the radiation image captured by said imaging unit is displayed on the display unit,
wherein if said discrimination unit discriminates at the start of radiation irradiation by said imaging unit that the imaging mode of the radiation image captured by said imaging unit is the mode of not storing the radiation image, said second decision unit decides the enlargement/reduction condition from the image size information and the image display region information such that the overall radiation image rotated under a rotation condition decided by said first decision unit is displayed at a maximum ratio with respect to the image display region.

2. The apparatus according to claim 1, wherein said first calculation unit calculates the image size information from information indicating a size of a detection region of a radiation detector.

3. The apparatus according to claim 1, wherein said first calculation unit calculates the image size information from information indicating a size of a radiation irradiation region adjusted by a collimator serving as a stop mechanism.

4. The apparatus according to claim 1, further comprising the storage unit, and wherein said storage unit stores the radiation image captured by said imaging unit, a rotation condition which has been decided by said first decision unit in previous radiation imaging and adjusted at the end of radiation imaging or after imaging, and an enlargement/reduction condition which has been decided by said second decision unit in previous radiation imaging and adjusted at the end of radiation imaging or after imaging.

5. The apparatus according to claim 4, wherein if said discrimination unit discriminates that the imaging mode of the radiation image captured by said imaging unit is the mode of not storing the radiation image in said storage unit at the start of radiation irradiation by said imaging unit, said first decision unit decides a rotation condition for the radiation image as the same condition as a rotation condition which has been stored in said storage unit and adjusted at the end of the radiation imaging or after imaging, and said second decision unit decides the enlargement/reduction condition from the image size information and the image display region information such that the overall radiation image is displayed within a corresponding number of pixels of the image display region at a maximum ratio with respect to the image display region.

6. The apparatus according to claim 5, wherein if said discrimination unit discriminates during radiation irradiation by said imaging unit that an imaging mode of the radiation image captured by said imaging unit is the mode of not storing the radiation image in said storage unit, said first decision unit decides the rotation condition in accordance with user operation input via an input unit, and said second decision unit decides the enlargement/reduction condition from the image size information and the image display region information such that the overall radiation image is displayed within the number of pixels of the image display region at a maximum ratio with respect to the image display region.

7. The apparatus according to claim 4, wherein the radiation imaging apparatus further comprises a third decision unit adapted to decide a panning condition for controlling panning display of displaying the radiation image while moving an image center in accordance with a discrimination result obtained by said discrimination unit, when displaying the radiation image on the display unit, wherein said storage unit further stores a panning condition which has been decided by said third decision unit in previous radiation imaging and adjusted at the end of radiation imaging or after imaging.

8. The apparatus according to claim 7, wherein if said discrimination unit discriminates that the imaging mode of the radiation image captured by said imaging unit at the start of radiation irradiation by said imaging unit is the mode of storing the radiation image in said storage unit, said first decision unit decides a rotation condition for the radiation image as the same condition as a rotation condition which has been stored in said storage unit and adjusted at the end of the radiation imaging or after imaging, said second decision unit decides the enlargement/reduction condition as the same condition as an enlargement/reduction condition which has been stored in said storage unit and adjusted at the end of the radiation imaging or after imaging, and said third decision unit decides the panning condition as the same condition as a panning condition which has been stored in said storage unit and adjusted at the end of the radiation imaging or after imaging.

9. The apparatus according to claim 8, wherein if said discrimination unit discriminates during radiation irradiation by said imaging unit that an imaging mode of the radiation image captured by said imaging unit is the mode of storing the radiation image in said storage unit, said first decision unit decides the rotation condition by user operation input via an input unit, said second decision unit decides the enlargement/reduction condition by user operation input via the input unit, and said third decision unit decides the panning condition by user operation input via the input unit.

10. The apparatus according to claim 8, wherein if said discrimination unit decides at the start of radiation irradiation in a moving image mode by said imaging unit that an imaging mode of the radiation image captured by said imaging unit is the mode of storing the radiation image in said storage unit, said first decision unit, said second decision unit, and said third decision unit respectively decide a rotation condition, an enlargement/reduction condition, and a panning condition as the same rotation condition, enlargement/reduction condition, and panning condition as a rotation condition, enlargement/reduction condition, and panning condition which have been adjusted at the end of radiation imaging in a previous moving image mode or after imaging.

11. The apparatus according to claim 10, wherein a type of moving image obtained by previous radiation imaging in a moving image mode is the same as that obtained by current radiation imaging in a moving image mode.

12. A radiation imaging method executed by a radiation imaging apparatus, the method comprising:
an imaging step of capturing a radiation image of an object;
a discrimination step of discriminating whether an imaging mode of the radiation image captured in said imaging step is a mode of storing the radiation image in a storage unit or a mode of not storing the radiation image in the storage unit;
a first calculation step of calculating image size information indicating a size of the radiation image;
a second calculation step of calculating image display region information indicating a size of an image display region in which the radiation image is configured to be displayed using a display unit;
a first decision step of deciding a rotation condition for rotation of the radiation image when the radiation image captured in said imaging step is displayed using the display unit; and
a second decision step of deciding an enlargement/reduction condition for display of the radiation image upon enlargement or reduction thereof when the radiation image captured in the imaging step is displayed using the display unit,
wherein if it is discriminated at the start of radiation irradiation in said imaging step in said discrimination step that the imaging mode of the radiation image captured in said imaging step is the mode of not storing the radiation image, the enlargement/reduction condition is decided in said second decision step from the image size information and the image display region information such that the overall radiation image rotated under a rotation condition decided in said first decision step is displayed at a maximum ratio with respect to the image display region.

13. A non-transitory computer-readable storage medium storing a program for causing a computer to execute the radiation imaging method defined in claim 12.

14. A radiation image processing apparatus comprising:
a display control unit adapted to display a captured radiation image in a display region;
a changing unit adapted to change a display form including one of a size and direction of the captured radiation image displayed by said display control unit;
a discrimination unit adapted to discriminate whether the captured radiation image falls within the display region after being changed by said changing unit; and
a limit processing unit adapted to limit a change made by said changing unit if the captured radiation image is an image captured in a mode of not storing the captured radiation image and said discrimination unit discriminates that the captured radiation image does not fall within the display region.

15. A radiation image processing method comprising:
- a display control step of displaying a captured radiation image in a display region;
- a changing step of changing a display form including one of a size and direction of the captured radiation image displayed in said display control step;
- a discrimination step of discriminating whether the captured radiation image falls within the display region after being changed in said changing step; and
- a limit processing step of limiting a change made in said changing step if the captured radiation image is an image captured in a mode of not storing the captured radiation image and it is discriminated in said discrimination step that the captured radiation image does not fall within the display region.

16. A non-transitory computer-readable storage medium storing a program for causing a computer to execute the radiation image processing method defined in claim 15.

17. A control apparatus for controlling of displaying a radiation image on a display unit obtained by a radiation imaging apparatus comprising:
- an obtaining unit configured to obtain the radiation image;
- a decision unit configured to decide a display condition by inheriting a display condition in a previous imaging form of the radiation imaging in a case where an imaging form of the obtained radiation image is a first form, and to decide a display condition so that a specific region of the radiation image is to be displayed on a display region of the display unit in a case where an imaging form of the obtained radiation image is a second form; and
- a display control unit configured to cause the display unit to display the radiation image based on the decided condition.

18. The control apparatus according to claim 17, wherein said decision unit decides a display condition that displays in a maximum size under the premise that the entire specific region of the radiation image imaged in the second form is to be displayed, and wherein said display control unit displays the radiation image enlarged or reduced based on the display condition.

19. The control apparatus according to claim 17, wherein the imaging form includes an imaging mode under the premise that a captured image is to be stored and an imaging mode under the premise that a captured image is not to be stored.

20. The control apparatus according to claim 17, wherein the imaging form includes at least one of fluoroscopy, cine, digital angiography (DA), or Digital Subtraction Angiography (DSA).

21. The control apparatus according to claim 17, wherein said decision unit inherits, for the radiation image imaged in the first form, a display condition of a radiation image imaged before the radiation image in the first form.

* * * * *